United States Patent
Kuhn et al.

(10) Patent No.: US 9,532,850 B2
(45) Date of Patent: Jan. 3, 2017

(54) PROCESS AND SYSTEM FOR CLEANING AND MAINTAINING AND FOR OPERATING A MEDICAL HAND-HELD INSTRUMENT

(75) Inventors: Bernhard Kuhn, Biberach (DE); Bernd Gugel, Ulm (DE); Thomas Braun, Biberach (DE)

(73) Assignee: KALTENBACH & VOIGT GMBH, Biberach (DE)

( * ) Notice: Subject to any disclaimer, the term of this patent is extended or adjusted under 35 U.S.C. 154(b) by 937 days.

(21) Appl. No.: 13/430,462

(22) Filed: Mar. 26, 2012

(65) Prior Publication Data

US 2012/0291814 A1 Nov. 22, 2012

(30) Foreign Application Priority Data

May 19, 2011 (DE) .......................... 10 2011 076 124

(51) Int. Cl.
| | | |
|---|---|---|
| *B08B 7/04* | (2006.01) | |
| *B08B 9/00* | (2006.01) | |
| *A61C 3/00* | (2006.01) | |
| *A61C 1/00* | (2006.01) | |
| *A61C 1/12* | (2006.01) | |
| *A61C 19/00* | (2006.01) | |
| *A61C 1/06* | (2006.01) | |

(52) U.S. Cl.
CPC ............... *A61C 1/0076* (2013.01); *A61C 1/12* (2013.01); *A61C 1/06* (2013.01); *A61C 19/002* (2013.01)

(58) Field of Classification Search
CPC ........... A61C 19/002; A61C 1/12; A61C 1/06; A61C 1/0076
See application file for complete search history.

(56) References Cited

U.S. PATENT DOCUMENTS

| 5,431,566 | A | * | 7/1995 | Blair et al. | 433/126 |
|---|---|---|---|---|---|
| 5,700,147 | A | * | 12/1997 | Mills et al. | 433/98 |
| 6,419,487 | B1 | * | 7/2002 | Tunnell et al. | 433/98 |
| 2006/0008765 | A1 | * | 1/2006 | Conners | 433/98 |
| 2009/0291410 | A1 | * | 11/2009 | Conners | 433/50 |

FOREIGN PATENT DOCUMENTS

| JP | 2003-235869 A | 8/2003 |
|---|---|---|
| JP | 3162151 U | 7/2010 |

OTHER PUBLICATIONS

Notice of Reasons for Rejection for Japanese Application No. 2012-114199, dated Jun. 13, 2013.

* cited by examiner

*Primary Examiner* — Alexander Markoff
(74) *Attorney, Agent, or Firm* — Marshall, Gerstein & Borun LLP

(57) ABSTRACT

A process and also to a system for cleaning and maintaining a medical hand-held instrument, in particular a dental hand-held instrument, with an elongate grip sleeve in which elements are arranged which pertain to a drive arrangement and which are, in particular, rotatably supported, for example a shaft. For the purpose of cleaning and maintaining the hand-held instrument different media are conducted through it. In this connection a first medium, for example oil, is conducted merely through a power-transmission region surrounding the elements of the drive arrangement, whereas, on the other hand, a second medium, for example a cleaning agent, is conducted additionally also through at least one further cavity within the hand-held instrument.

8 Claims, 6 Drawing Sheets

PROCESS AND SYSTEM FOR CLEANING AND MAINTAINING AND FOR OPERATING A MEDICAL HAND-HELD INSTRUMENT

BACKGROUND OF THE INVENTION

Field of the Invention

The invention relates to a process for cleaning and maintaining a medical hand-held instrument, in particular a dental hand-held instrument, that exhibits an elongate grip sleeve in which elements are arranged which pertain to a drive arrangement and which are, in particular, rotatably supported, wherein for the purpose of cleaning and maintaining the hand-held instrument different media are conducted through it. The invention relates furthermore to a system for cleaning and maintaining a medical hand-held instrument, in particular a dental hand-held instrument, that exhibits an elongate grip sleeve in which elements are arranged which pertain to a drive arrangement and which are, in particular, rotatably supported, the system being designed, for the purpose of cleaning and maintaining the hand-held instrument, to conduct different media through it. The invention relates furthermore to a process and a system for operating a medical hand-held instrument, in particular a dental hand-held instrument, that exhibits an elongate grip sleeve in which elements are arranged which pertain to a drive arrangement and which are, in particular, rotatably supported.

Related Technology

For the purpose of cleaning and maintaining a corresponding dental hand-held instrument in the form of an anglepiece it is known to clean the rotatably supported elements of the drive arrangement with a cleaning agent or cleaning fluid in a first step and to lubricate or oil them in a subsequent, second step. In this process the cleaning agent and the oil are conducted through cavity regions of the anglepiece that extend directly around rotatably supported elements of the drive arrangement. The anglepiece includes, besides these cavity regions which are perfused by the cleaning agent and the oil, yet further cavity regions, which are connected to the external space of the anglepiece via jointing gaps. These further cavity regions are connected to one another by a light-means guide, a coolant guide and ducts for sensor lines and power lines and at the same time are almost hermetically shielded or separated from the first-named cavity regions perfused by the cleaning agent and the oil. With the known process for cleaning and maintenance, the further cavity regions are consequently not treated. There is therefore a risk that pathogens, for example viruses, that have penetrated into the further cavity regions within the scope of a dental application of the anglepiece will not be removed from the anglepiece by the cleaning and maintenance and will subsequently allow a risk of infection to arise for users and patients.

SUMMARY OF THE INVENTION

The invention improves a corresponding process or system for cleaning and maintaining a medical hand-held instrument, in particular a dental hand-held instrument. In particular, avoidance or at least reduction of internal microbial contamination or soiling of a corresponding hand-held instrument made possible by the invention.

According to the invention, a process is provided for cleaning and maintaining a medical hand-held instrument, in particular a dental hand-held instrument, that exhibits an elongate grip sleeve in which elements are arranged which pertain to a drive arrangement and which are, in particular, rotatably supported, wherein for the purpose of cleaning and maintaining the hand-held instrument different media are conducted through it. In this process a first medium is conducted merely through a power-transmission region surrounding the elements of the drive arrangement, whereas, on the other hand, a second medium is conducted additionally also through at least one further cavity within the hand-held instrument.

By virtue of the conduction of the second medium through the further cavity, a cleaning of the further cavity and consequently an improved cleaning of the hand-held instrument overall is made possible.

In the case of the power-transmission region which surrounds the elements of the drive arrangement it may be a question of a cavity region of the hand-held instrument that extends directly around at least one rotatably supported element of the drive arrangement, for example a shaft. In the case of the at least one further cavity it may be a question of further cavity regions of the hand-held instrument that are connected to the external space of the hand-held instrument via at least one jointing gap and at the same time are connected to one another, for example by a light-means guide and/or a coolant guide and/or at least one duct for sensor lines and/or power lines.

In the case of the first medium it is preferably a question of an agent for lubricating the elements of the drive arrangement, for example an oil or an oil dispersion, and in the case of the second medium it is preferably a question of a cleaning agent, in particular a cleaning fluid. By means of the cleaning agent it is possible, in particular, for germs to be removed from the further cavity.

Advantageously the power-transmission region is in communication with the further cavity, this connection being bridged when the first medium is being conducted through. In particular, in the course of conducting the first medium through the power-transmission region the connection for the first medium can be kept closed. As a result, it is made possible that the first medium does not enter the further cavity. In particular, in this way the situation can be avoided where oil enters the further cavity and subsequently gets through the at least one jointing gap onto an external surface of the hand-held instrument and consequently, for example, fouls a grip region of the hand-held instrument with oil.

The media are preferably withdrawn from various supply containers, in which case attachment regions of the supply containers, via which the corresponding medium is conducted into the hand-held instrument, are differently configured. By appropriate differing configuration of the attachment regions it is possible, in particular, to ensure that the connection is closed by an attachment of a first storage container, which contains the first medium, and the connection is not closed by an attachment of a second storage container, which contains the second medium. As a result, the process becomes more reliable, and in addition the corresponding system is simplified.

According to a second aspect of the invention a system is provided for cleaning and maintaining a medical hand-held instrument, in particular a dental hand-held instrument, that exhibits an elongate grip sleeve in which elements are arranged which pertain to a drive arrangement and which are, in particular, rotatably supported. In this connection, for the purpose of cleaning and maintaining the hand-held instrument the system is designed to conduct different media through the instrument. The system is furthermore designed so that a first medium is conducted merely through a power-transmission region surrounding the elements of the drive arrangement, whereas, on the other hand, a second medium is additionally also conducted through at least one further cavity within the hand-held instrument.

In the case of the first medium it is preferably a question of an agent for lubricating the elements of the drive arrangement, and in the case of the second medium it is preferably a question of a cleaning agent.

The power-transmission region is advantageously in communication with the further cavity, the system being designed so that this connection is bridged when the first medium is being conducted through.

The system preferably includes various storage containers for the media, in which case attachment regions of the storage containers, via which the corresponding medium is conducted into the hand-held instrument, are differently configured.

According to a third aspect of the invention a combination is provided, including or consisting of a system according to the invention and a medical hand-held instrument, in particular a dental hand-held instrument. In this case the hand-held instrument preferably exhibits a connecting duct between the power-transmission region and the further cavity.

According to a fourth aspect of the invention a process is provided for operating a medical hand-held instrument, in particular a dental hand-held instrument, that exhibits an elongate grip sleeve in which elements are arranged which pertain to a drive arrangement and which are, in particular, rotatably supported. In this process a gaseous, preferably sterile or pure, medium is conducted, propelled by an excess pressure, through a power-transmission region surrounding the elements of the drive arrangement.

As a result, it is possible for a penetration of germs and/or dirt into the hand-held instrument to be prevented or at least lessened.

The medium is preferably antiseptic. As a result, it is possible for a particularly marked abatement of germs to be achieved.

Advantageously, a lower and/or upper limit for the excess pressure is/are defined in advance. As a result, it is possible for a particularly good ratio of the effort for generating the excess pressure to the effect for the purpose of germ abatement to be achieved. The lower limit preferably amounts to between 1 hPa and 10 hPa, for example 5 hPa.

A corresponding system is furthermore provided for operating a medical hand-held instrument, in particular a dental hand-held instrument, that exhibits an elongate grip sleeve in which elements are arranged which pertain to a drive arrangement and which are, in particular, rotatably supported. The system exhibits means for conducting a gaseous, preferably sterile or pure, medium, propelled by an excess pressure, through a power-transmission region surrounding the elements of the drive arrangement.

The system is preferably designed to maintain the excess pressure on medical or dental instruments in permanently constant manner during an operation or over a relatively long period of time in the dental or surgical practice. The excess pressure can be initiated when the instruments or consultation rooms are put into operation.

BRIEF DESCRIPTION OF THE DRAWINGS

The invention is described in greater detail below on the basis of an embodiment and with reference to the drawings. Shown are.

DETAILED DESCRIPTION

Figure 1:
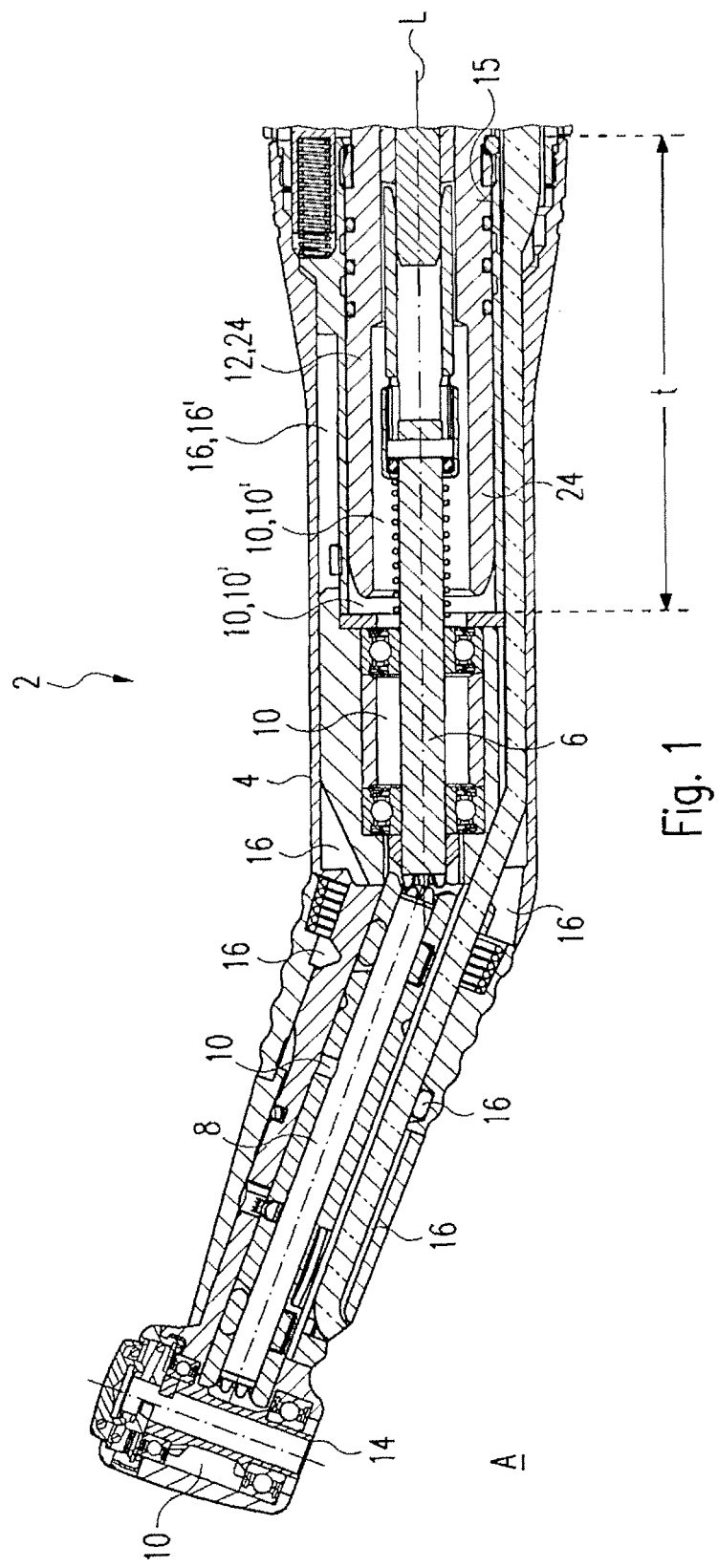
FIG. 1 a cross section through a dental anglepiece, fitted onto a peg-shaped coupling element of a motor element (only partly shown), FIG. 2 a detail from a cross section of a further dental anglepiece mounted onto a motor element, FIG. 3 a cross section corresponding to FIG. 2, wherein the anglepiece has been mounted onto, for example, a lubricant spray can, FIG. 4 a cross section corresponding to FIG. 2, wherein the anglepiece has been mounted onto, for example, an attachment region of a maintenance machine, FIG. 5 a cross section corresponding to FIG. 2, wherein the anglepiece has been mounted onto, for example, a cleaning-fluid spray can, and FIG. 6 a sketch relating to a further aspect of the invention, according to which a gaseous, preferably sterile medium, for example a gaseously sterile or gaseously pure or gaseously antiseptic medium, is conducted through the hand-held instrument.

For the purpose of describing the invention, to begin with in FIG. 1 a hand-held instrument 2 is shown in exemplary manner sketched in cross section in the form of a dental anglepiece. The hand-held instrument 2 exhibits an elongate grip sleeve 4.

As is the case in the example shown, the hand-held instrument 2 may be provided for the purpose of driving a rotating tool (not sketched in FIG. 1), for example a drill. For this purpose the hand-held instrument 2 may exhibit a tool outlet opening 14 or, to be more exact, a drill outlet opening.

For the purpose of driving the tool there may be provision, in particular, that the hand-held instrument 2 is brought into driving connection with a motor element 12, for example an electric-motor element, in particular by fitting the hand-held instrument 2 onto a coupling of the motor element 12. In FIG. 1 merely an anterior region of the motor element 12 has been sketched; this may be a peg-shaped coupling element 24 which, for example, exhibits an approximately annular-cylindrical wall region. The hand-held instrument 2 may exhibit a rear recess or, to be more exact, a recess formed on the end region, situated opposite the tool outlet opening 14, of the hand-held instrument 2, in the form of a coupling socket 15 which has accordingly been designed to receive the coupling element 24 of the motor element 12.

In the grip sleeve 4 there are arranged elements pertaining to a drive arrangement, in particular rotatably supported elements, for example a shaft 6 and a further shaft 8. The rotatably supported elements may be designed, in particular, for a transmission of power from the motor element 12 to the tool.

By virtue of the elongate shape—at least in a region of the hand-held instrument 2 situated opposite the tool outlet opening 14 or, to be more exact, in a "rear" region—of the grip sleeve 4, it is possible for a longitudinal axis L of the hand-held instrument 2 to be defined. The coupling socket 15 may—as shown in the Figures in exemplary manner—be formed extending parallel to this longitudinal axis L or extending around the longitudinal axis L. As shown, the coupling socket 15 may exhibit a depth t with respect to the longitudinal axis L.

The hand-held instrument 2 exhibits a power-transmission region 10 surrounding the elements of the drive arrangement. In this connection it may be a question, in particular, of a cavity region that extends directly around at least one rotatably supported element of the drive arrangement, that is to say, for example, around the shaft 6 and/or around the further shaft 8. In FIG. 1 several portions of the power-transmission region 10 are denoted by reference symbol 10. As is the case in the example shown, the power-transmission region may extend from the coupling socket 15 continuously as far as the tool outlet opening 14.

As is the case in the example shown, one of the rotatably supported elements, here the shaft 6, may extend into the coupling socket 15, so that the power-transmission region 10 extends partly within the region circumscribed by the coupling socket 15. In FIG. 1 this part of the power-transmission region 10 is additionally denoted by reference symbol 10'.

Ordinarily, in a normal operation of the hand-held instrument 2 cooling air or inhibiting air emanating from the motor element 12 is conducted as far as the tool outlet opening 14 of the hand-held instrument 2, specifically in such a manner that, by this means, an excess pressure is generated in the power-transmission region 10. In this way a penetration of dirt or germs into the power-transmission region 10 during the work is to be prevented.

From the state of the art in this respect, for the purpose of cleaning and maintaining the hand-held instrument 2 it is known to conduct different media through it. In this process, in a first step a cleaning liquid is conducted through the power-transmission region 10, and in a following step an oil or an oil dispersion.

The hand-held instrument 2 furthermore exhibits a further cavity 16. In the case of the latter it may be a question of further cavity regions of the hand-held instrument 2 which are connected to the external space A of the hand-held instrument 2 via at least one jointing gap and at the same time are connected to one another, for example by a light-means guide and/or a coolant guide and/or at last one duct for sensor lines and/or power lines. In the case of the further cavity 16 it may be a question, in particular, of a further cavity region that does not immediately border an element, in particular a rotatably supported element of the drive arrangement. In the case of the further cavity 16 it may be a question of a dead space.

As is the case in the example shown, the further cavity 16 may include a part, denoted additionally in FIG. 1 by 16', which extends radially outside the coupling socket 15 with respect to the longitudinal axis L.

In accordance with the prior art a cleaning of the further cavity 16 is not provided, so that within the scope of a treatment application of the hand-held instrument 2 it may happen that dirt or germs penetrate(s) through the at least one jointing gap into the further cavity 16 and is/are not caught hold of and dragged along in the course of a following cleaning and maintenance, that is to say, they remain in the further cavity 16. As a result of this, a potential danger of infection is created, both for a user of the hand-held instrument 2 and for a patient who is being treated with the hand-held instrument 2.

According to the invention there is provision that, for the purpose of cleaning and for the purpose of maintenance, a first medium, in particular an agent for lubricating the elements of the drive arrangement, for example an oil or an oil dispersion, is conducted merely through the power-transmission region 10, that is to say, in particular not through the further cavity 16. A second medium, on the other hand, in particular a cleaning agent, is additionally also conducted through the at least one further cavity 16 within the hand-held instrument 2. As a result, a cleaning of the further cavity 16 is made possible.

In particular, there may accordingly be provision that in a first step for cleaning the hand-held instrument 2 the second medium (in particular, cleaning agent) is conducted both through the power-transmission region 10 and through the further cavity 16, and in a following step, in particular in an immediately ensuing step, the first medium (in particular, oil or oil dispersion) is conducted merely through the power-transmission region 10, that is to say, in particular not through the further cavity 16. In this way it is possible to avoid the situation where the first medium subsequently escapes through the at least one jointing gap and by this means wets or fouls with oil the surface of the hand-held instrument 2.

Figure 2:
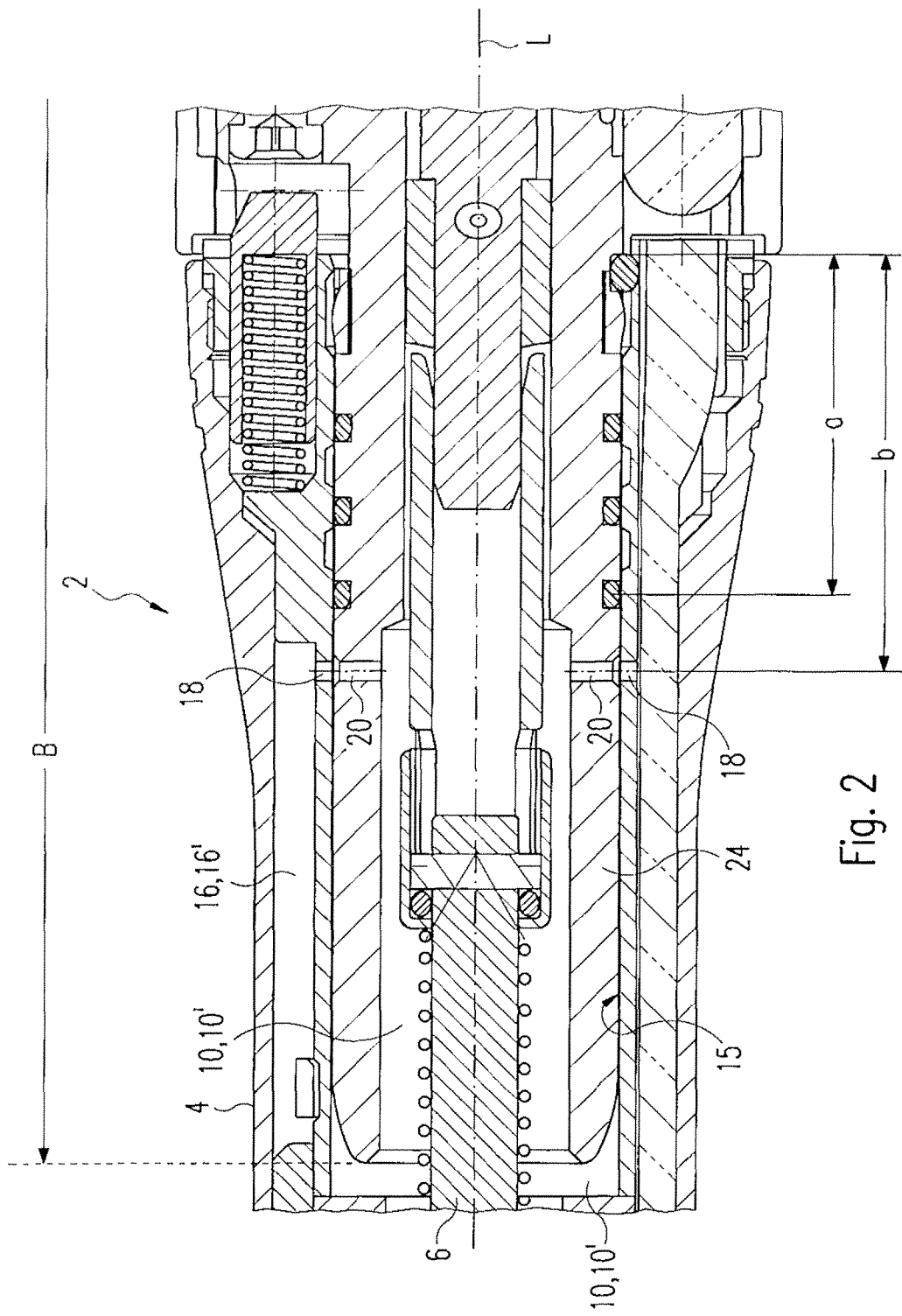

Advantageously the power-transmission region 10 is in communication with the further cavity 16. In FIG. 2 a connection of such a type is shown in exemplary manner. For this purpose the hand-held instrument 2 may exhibit at least one connecting duct 18 which is preferably designed in such a way that it connects the coupling socket 15 to the further cavity 16 in such a manner that the second medium (cleaning agent) perfusing this connecting duct 18 can penetrate into the further cavity 16. The connection may accordingly be constituted by the at least one connecting duct 18.

In the example shown the connecting duct 18 is formed running radially outwards with respect to the longitudinal axis L at a depth b of the coupling socket 15 and leads into the part of the further cavity 16 denoted additionally by reference symbol 16'. As a result, it is possible to design the connecting duct 18 to be particularly short. At a depth a of the coupling socket 15, which is smaller than depth b, in the example shown the anterior seal of a cooling-air guide is formed. (In the hand-held instrument 2 sketched in FIG. 1 the connecting duct 18 has not been sketched.)

The hand-held instrument 2 is preferably designed in such a manner that the at least one connecting duct 18 constitutes the only possible transition-point at which the second medium (cleaning agent) coming from the power-transmission region 10 can penetrate into the further cavity 16. Apart from the at least one connecting duct 18, advantageously the further cavity 16 is accordingly designed to be at least practically or almost hermetically shielded or separated from the power-transmission region 10.

The at least one connecting duct 18 is advantageously formed, with respect to the longitudinal axis L of the hand-held instrument 2, within that region B via which the coupling of the motor element 12 or, to be more exact, the peg-shaped coupling element 24 extends when the hand-held instrument 2 has been fitted onto the motor element 12 or the coupling thereof, as provided for the driving connection.

In order to enable a passage or flow of the second medium (cleaning agent) from the power-transmission region 10 to the further cavity 16 with motor element 12 fitted, in the motor element 12, in particular in the peg-shaped coupling element 24 or in the annular-cylindrical wall region thereof, at least one opening 20 may be provided which is designed in such a manner that the second medium (cleaning agent) can flow from the at least one opening 20 into the at least one connecting duct 18 and subsequently into the further cavity 16 when the hand-held instrument 2 is fitted, as provided for, on the motor element 12 or on the coupling element 24 thereof.

By virtue of the connection that has been described and the motor element 12 with the at least one opening 20, it is made possible that in a normal operation of the hand-held instrument 2 cooling air or inhibiting air emanating from the motor element 12 also infiltrates the further cavity 16 and consequently counteracts a penetration of dirt or germs into the further cavity 16.

For the purpose of maintaining the hand-held instrument 2, the stated connection is preferably bridged or kept closed when the first medium (oil, oil dispersion) is being conducted through. In this way, in particularly simple manner it is possible for the situation to be avoided where the first medium (oil, oil dispersion) enters the further cavity 16 and subsequently gets through the at least one jointing gap onto an outer surface of the hand-held instrument 2.

For this purpose there may advantageously be provision that the media are withdrawn from various storage containers, in which case attachment regions of the storage containers, via which the corresponding medium is conducted into the hand-held instrument 2, are differently configured.

In particular, for the purpose of maintenance there may be provision that use is made of a first storage container which contains the first medium (oil, oil dispersion) and which exhibits a first attachment region which is designed to be inserted into the coupling socket 15 of the hand-held instrument 2 in such a manner that it closes the connection or, to be more exact, the connecting duct 18 and at the same time enables an outflow of the first medium into the power-transmission region 10. For the purpose of cleaning, there may be provision that use is made of a second storage container which contains the second medium (cleaning agent) and which exhibits a second attachment region which is designed to be inserted into the coupling socket 15 of the hand-held instrument 2 in such a manner that it does not close the connection or, to be more exact, the connecting duct 18' and at the same time enables an outflow of the second medium both into the power-transmission region 10 and into the further cavity 16.

Figure 3:
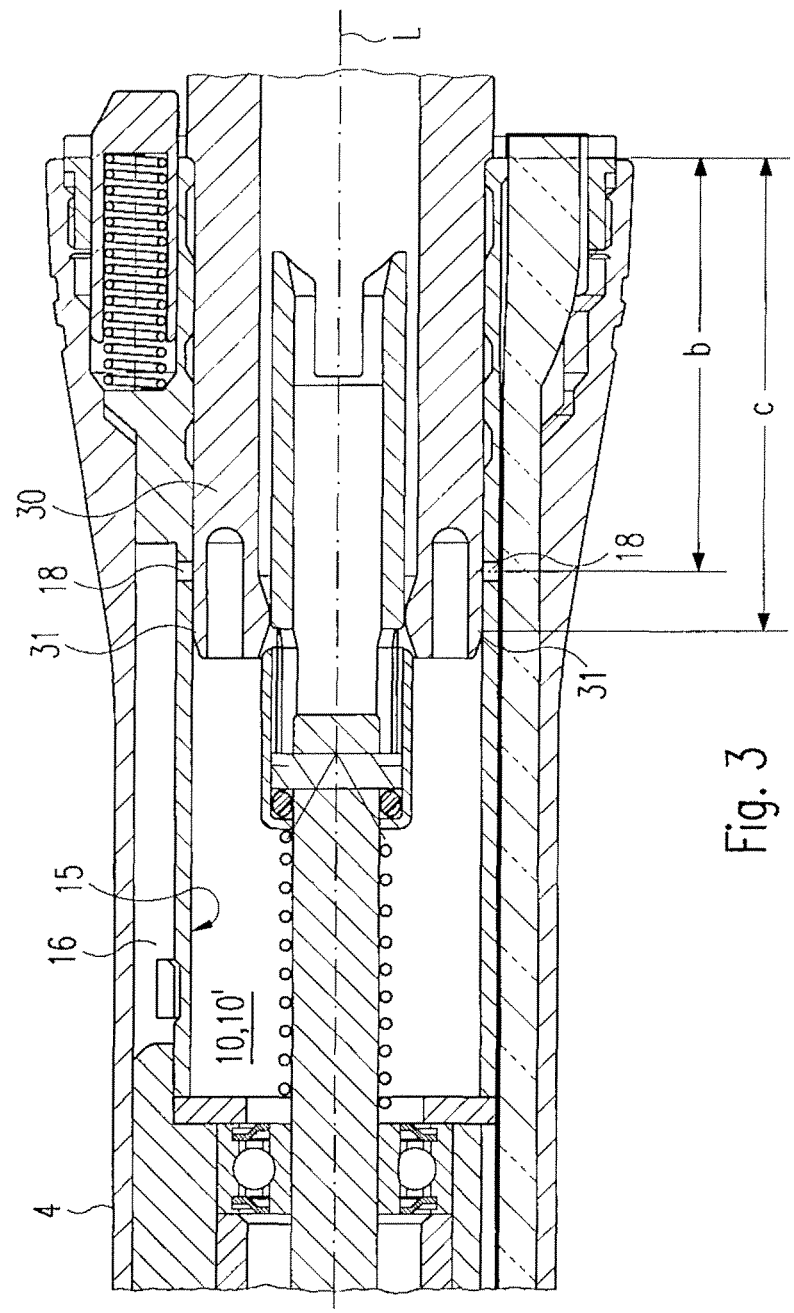

In FIG. 3 such a first attachment region 30 of a first storage container has been sketched in exemplary manner in the form of a spray can (not shown as a whole). The first attachment region 30 preferably exhibits—in the fitted state—with respect to the longitudinal axis L at a depth c of the coupling socket 15 a seal 31, for example in the form of a can nipple, by virtue of which a closure of the connection or, to be more exact, of the connecting duct 18 is guaranteed. Depth c is greater than the aforementioned depth b at which the connecting duct 18 is located, by virtue of which a particularly simple and reliable closure of the connection by the first attachment region 30 is made possible.

Figure 4:
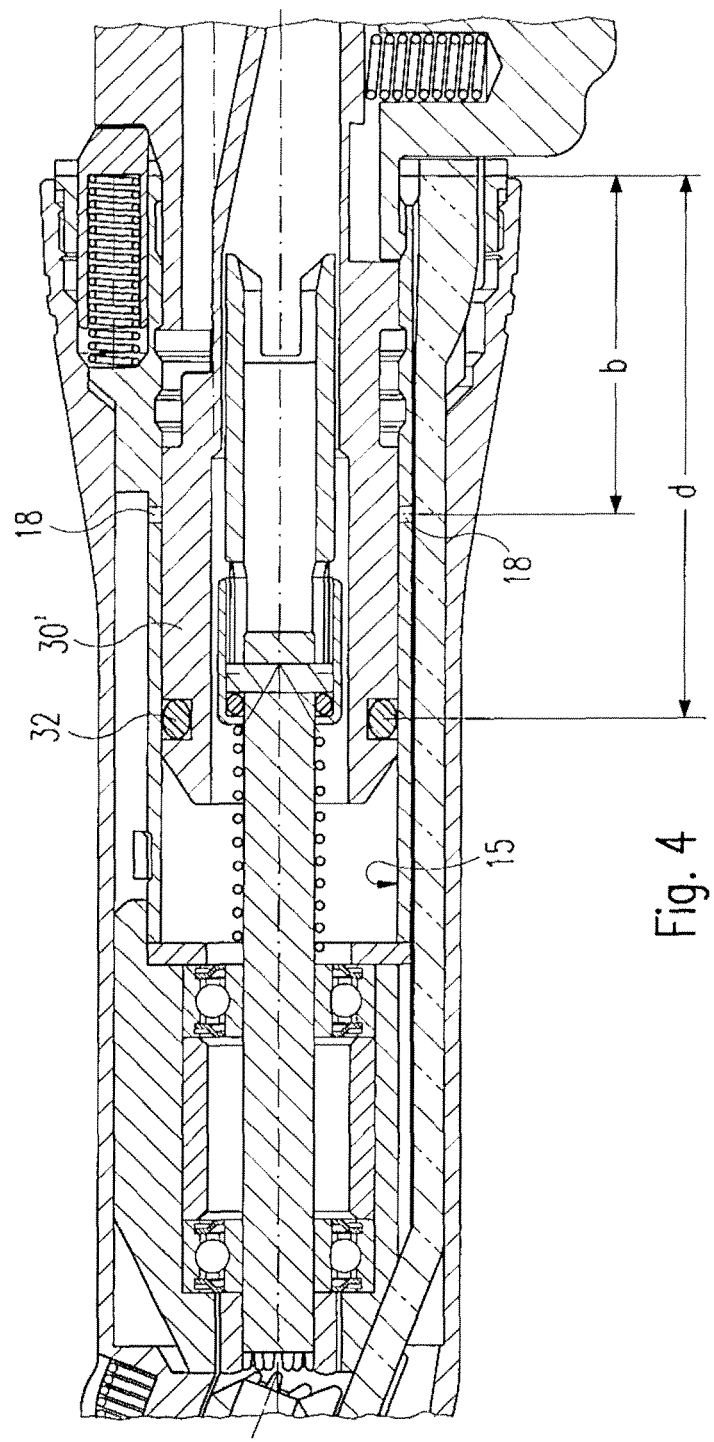

In FIG. 4 a further example of a first attachment region 30' has been sketched which at a depth d exhibits a seal 32 in the form of a ring seal in relation to the coupling socket 15 or the inner wall thereof, depth d again being greater, corresponding to the above remarks, than depth b at which the connecting duct 18 is located.

Figure 5:
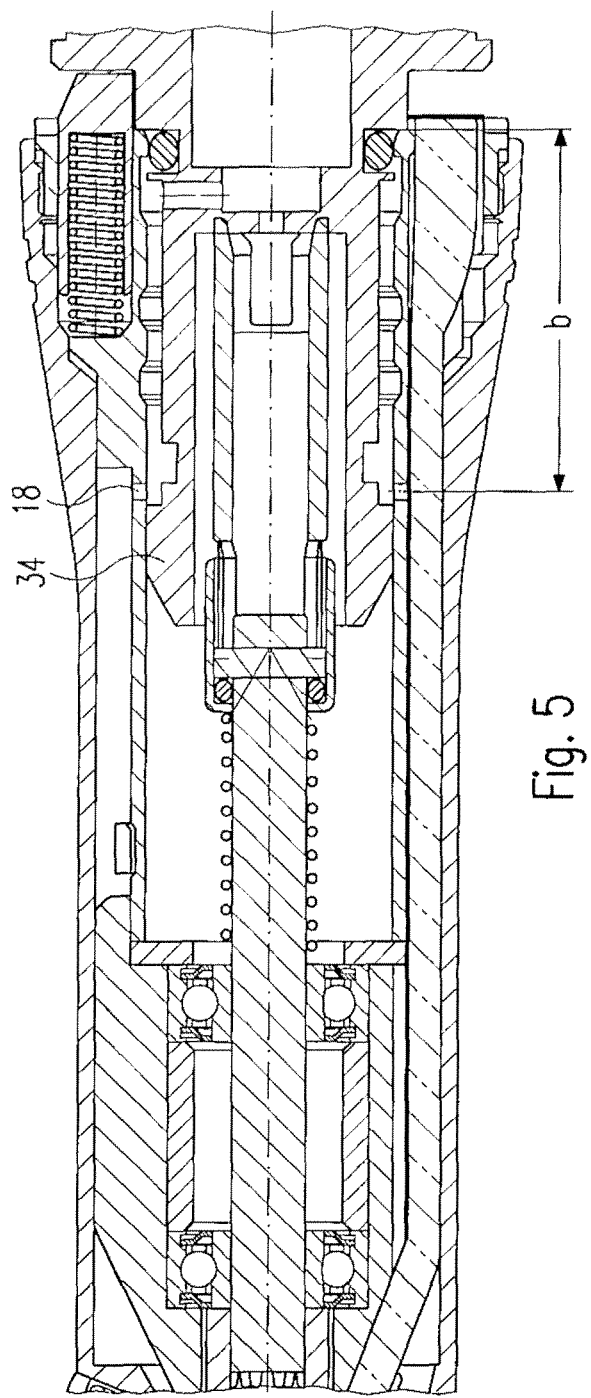

In FIG. 5 a second attachment region 34 of a second storage container has been sketched in exemplary manner in the form of a further spray can containing cleaning agent. The second attachment region 34 exhibits a first exit region for the second medium (cleaning agent), which leads directly to the at least one connecting duct 18, and a second exit region for the second medium, which leads directly to the power-transmission region 10. So if the second attachment region 34 has been inserted, as provided for, into the coupling socket 15, the connection or, to be more exact, the connecting duct 18 is not closed by this means, and the second medium can flow out of the second storage container both into the power-transmission region 10 and into the second cavity 16, in order to flush both the stated spaces 10, 16.

A system according to the invention for cleaning and maintaining the medical hand-held instrument 2 is designed, in the sense of the above description, to conduct different media through the hand-held instrument 2 for the purpose of cleaning and maintaining it, whereby the first medium is conducted merely through the power-transmission region 10, whereas, on the other hand, the second medium is additionally also conducted through the further cavity 16 within the hand-held instrument 2. The system accordingly exhibits appropriate means for conducting the stated media through the hand-held instrument 2.

The system advantageously includes the stated various storage containers for the media, in which case attachment regions of the storage containers, via which the corresponding medium is conducted into the hand-held instrument 2, are differently configured. In particular, the system may accordingly exhibit the first storage container, described above, for the first medium, which exhibits the first attachment region 30 or 30', as well as the second storage container, described above, for the second medium, which exhibits the second attachment region 34.

The system may advantageously be combined with the hand-held instrument 2 described above to yield a combination according to the invention, in which case the hand-held instrument 2 enables the connection described above, that is to say, it exhibits, for example, the connecting duct 18. Furthermore, the system or the combination may accordingly advantageously include the motor element 12, the coupling element 24 of which exhibits the at least one opening 20.

In the course of operating surgical handpieces and angle-pieces, in accordance with the state of the art the use of cooling air or inhibiting air is deliberately dispensed with, in order to prevent a microbial contamination of the treatment region in question with contaminated air. But precisely in the case of surgical hand-held instruments of such a type there is a particularly high risk of a penetration by body fluids and also by saline solution. These hand-held instruments are accordingly soiled particularly intensely during a treatment of a patient and therefore have to be reconditioned or cleaned and maintained with particularly great effort.

Figure 6:
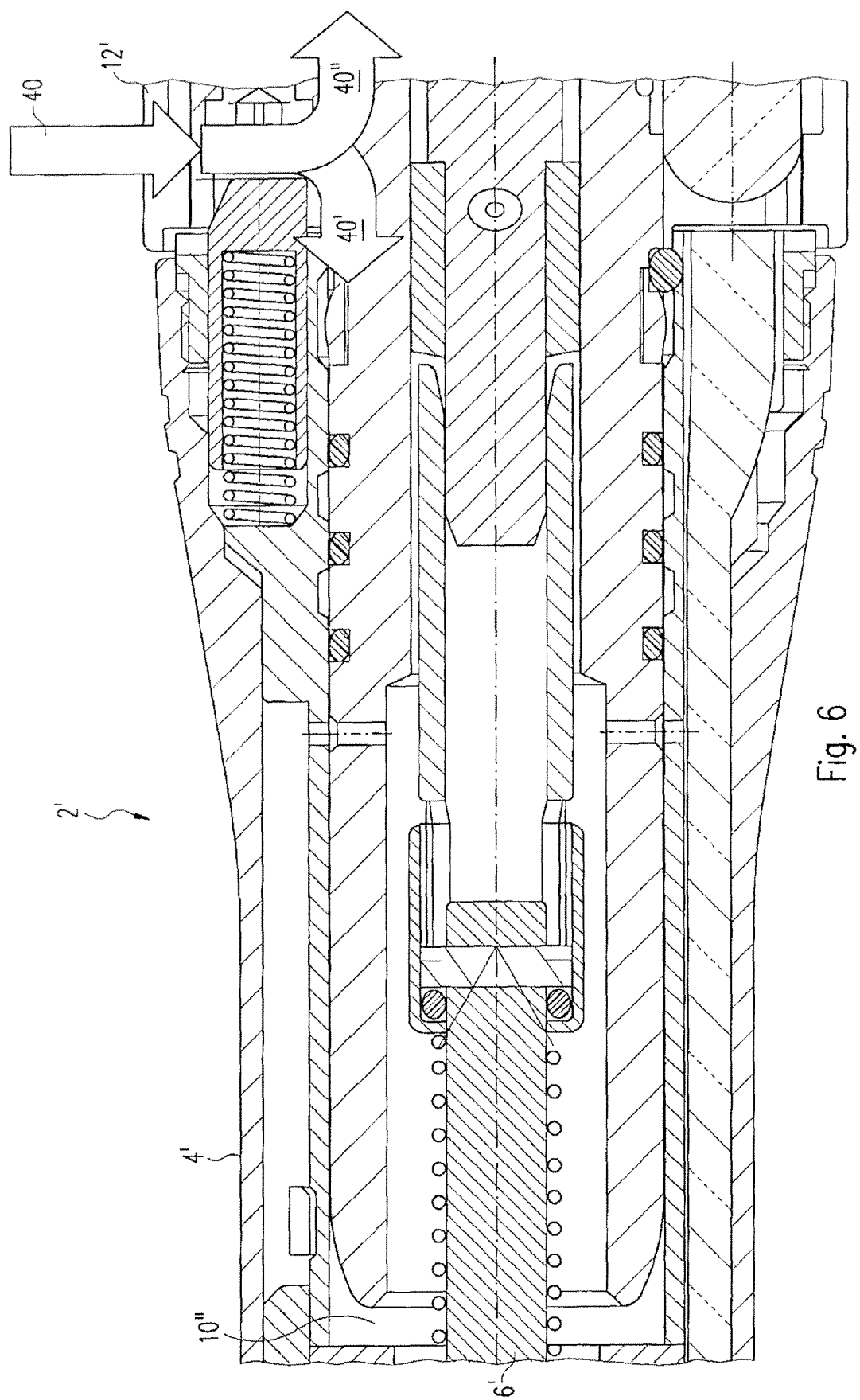

According to a further aspect of the invention, in the course of operating a corresponding handpiece 2', sketched in FIG. 6 in a section, which exhibits an elongate grip sleeve 4' in which elements 6' are arranged which pertain to a drive arrangement and which are, in particular, rotatably supported, a gaseous, sterile medium is conducted, propelled by an excess pressure, through a power-transmission region 10" surrounding the elements of the drive arrangement. In this way it is possible for the soiling of the hand-held instrument 2' to be significantly reduced. In the case of the medium it may be a question, in particular, of inhibiting air.

Particularly in the case of a surgical application, the conduction of the medium during a surgical treatment may be activated continuously. This reduces the microbial contamination still further.

In the case of the medium it is preferably a question of an antiseptic medium, by virtue of which a more extensive reduction of the bacterial count can be achieved.

Preferably a lower and/or upper limit for the excess pressure is/are defined in advance. The lower limit may be defined as a function of a protective action that is deemed necessary as a minimum. It may preferably amount to between 1 hPa and 10 hPa, for example 5 hPa. A polluted liquid that does not exceed this pressure cannot then penetrate into the hand-held instrument 2'.

The upper limit for the excess pressure may be defined as a function of the following factors: medical hazard, disturbing generation of noise, disturbing feeling of the patient and/or of the treating person of being exposed to a flow, in particular as a result of cooling or drying up, technical limit (supply). Preferably an excess-pressure valve for the medium may also have been provided or may be provided on the hand-held instrument 2', this valve being designed in such a manner that it opens in the case of an exceeding of the or an upper limit of the excess pressure. In this way, corresponding damage to the patient can, in particular, be prevented.

As indicated in FIG. 6 by the arrow 40, for the purpose of supplying the medium into the hand-held instrument 2' there may be provision that a (separate) sterile hose, possibly usable only once, is fitted in the region of a coupling of a corresponding motor element 12'. Subsequently the sterile medium, for example filtered air, can be switched in, so that it flows in through the hose. Furthermore, the hand-held instrument 2', already sterilized beforehand, can—in the case of inflowing medium—be fitted and brought into the driving connection provided for. During the subsequent operation the supply of the medium under excess pressure remains constantly switched on, so that no germs can penetrate. Since in the event of a soiling in this case it may only be a question of a more or less intense external soiling, a subsequent reconditioning is possible with distinctly less effort.

The medium or the inhibiting air attached to the coupling-point will—as indicated by the arrow 40'—for the most part exit towards the front and—as indicated by the arrow 40"—to a lesser extent towards the rear. Germs that are possibly present in a not absolutely sterile motor are carried away from the site of the operation together with the medium. The hose and the motor element 12' would then not need to satisfy the most stringent antiseptic requirements.

The quantity of the perfusing medium can be kept very small, since only a slight excess pressure is required. The quantity can be chosen in such a manner that a disturbing noise is practically not generated, or at least not noticeably.

There may also be provision that the inhibiting air perfuses the hand-held instrument perpetually for an entire day. A microbial contamination can then occur only on external surfaces, and the latter can be kept relatively germ-free by simple wiping, if need be.

There is preferably provision that the medium or the inhibiting air, as described above in connection with the "second medium", is conducted both through the power-transmission region and through the further cavity, particularly preferably through all the cavities of the hand-held instrument.

A corresponding system for operating the medical hand-held instrument, in particular the dental hand-held instrument 2', exhibits, in the sense of the above description, means for conducting the gaseous, sterile medium, propelled by an excess pressure, through the power-transmission region surrounding the elements of the drive arrangement. The system is preferably designed to conduct the medium also through an appropriate further cavity, particularly preferably through all the cavities of the hand-held instrument.

Furthermore, the aforementioned hose or an appropriate hose attachment may be provided, for example on the motor element 12'.

To be mentioned, furthermore, is the fact that the invention is also advantageous with respect to the sanitary condition and cleanliness of corresponding hand-held instruments in connection with its effect on the service lives of components and structures of the hand-held instruments that are subjected to wear, such as, for example, ball bearings, friction-points etc. By utilizing air that has been cleaned by a particle filter, it is possible in this way for an increase in the service lives of corresponding components and structures to be achieved. This holds, in particular, also in the case of dental instruments; since the latter are exposed in practice to particularly high dust loadings, this aspect is of particular significance in this context.

The invention claimed is:

1. A medical hand-held instrument, comprising:
   an instrument having an elongate grip sleeve in which drive arrangement elements are arranged and supported,
   a cavity that is fluidly connected to a power-transmission region, the cavity being separated from, and extending radially outside of, a coupling socket,
   a coupling element for coupling the medical hand-held instrument to a motor element, the coupling element being at least partially disposed in the coupling socket, the coupling element including an opening in a wall thereof; and
   a connecting duct that fluidly connects the cavity to the coupling socket, the connecting duct running radially outwardly,
   wherein the opening in the coupling element wall is substantially aligned with the connecting duct when the coupling element is disposed in the coupling socket.

2. The medical hand-held instrument according to claim 1, wherein the medical hand-held instrument is a dental hand-held instrument.

3. The medical hand-held instrument according to claim 1, wherein the drive arrangement elements are rotatably supported in the elongate grip sleeve.

4. The medical hand-held instrument according to claim 1, wherein the connecting duct is formed running radially outwards with respect to a longitudinal axis of the elongate grip sleeve.

5. The medical hand-held instrument according to claim 4, further comprising a gaseous medium flowing through the connecting duct from the power transmission region to the cavity.

6. The medical hand-held instrument according to claim 4, wherein the connecting duct is formed within a region into which the coupling element extends into the elongate grip sleeve when the elongate grip sleeve is connected to the motor element.

7. The medical hand-held instrument according to claim 1, the instrument further including a means for maintaining a gaseous medium within the elongate grip sleeve at an excess pressure.

8. The medical hand-held instrument according to claim 7, wherein a lower value of the excess pressure is between 1 hPa and 10 hPa.

* * * * *